US010564073B2

(12) United States Patent
Hoff

(10) Patent No.: US 10,564,073 B2
(45) Date of Patent: Feb. 18, 2020

(54) INSERT FOR AN INFLOW AND OUTFLOW APPARATUS

(71) Applicant: DEUTSCHER WETTERDIENST, Offenbach (DE)

(72) Inventor: Axel Hoff, Hannover (DE)

(73) Assignee: Bundesrepublik Deutschland, vertreten durch das BMVI, dieses vertreten durch den Deutschen Wetterdienst (DE)

( * ) Notice: Subject to any disclaimer, the term of this patent is extended or adjusted under 35 U.S.C. 154(b) by 267 days.

(21) Appl. No.: 15/529,138

(22) PCT Filed: Nov. 24, 2015

(86) PCT No.: PCT/EP2015/077573
§ 371 (c)(1),
(2) Date: May 24, 2017

(87) PCT Pub. No.: WO2016/083422
PCT Pub. Date: Jun. 2, 2016

(65) Prior Publication Data
US 2017/0261409 A1    Sep. 14, 2017

(30) Foreign Application Priority Data
Nov. 24, 2014  (EP) .................................... 14194585

(51) Int. Cl.
*G01N 1/22*   (2006.01)
*B64D 47/00*  (2006.01)
(Continued)

(52) U.S. Cl.
CPC .......... *G01N 1/2273* (2013.01); *B64D 47/00* (2013.01); *G01N 21/05* (2013.01); *G01N 21/27* (2013.01);
(Continued)

(58) Field of Classification Search
CPC ................. G01N 1/2773; G01N 21/05; G01N 2001/2279; G01N 2001/2285; B64D 47/00
(Continued)

(56) References Cited

U.S. PATENT DOCUMENTS 4,092,123 A    5/1978   Vancheri et al.
6,857,328 B1   2/2005   Spurgeon
(Continued)

FOREIGN PATENT DOCUMENTS

CN    101437580 A    5/2009
CN    102252875 A    11/2011
(Continued)

OTHER PUBLICATIONS

M. Hermann, et al; "Sampling Characteristics of an Aircraft-Borne Eerosol Inlet System"; Journal of Atmospheric and Oceanic Technology; vol. 18; Jan. 2001; pp. 7-19.
(Continued)

*Primary Examiner* — Benjamin R Schmitt
(74) *Attorney, Agent, or Firm* — Ware, Fressola, Maguire & Barber LLP

(57) ABSTRACT

An aircraft-mountable inflow and outflow apparatus has an accumulating sleeve, an inflow line and at least one exit opening. The regulating sleeve has an entry opening. The inflow line has a supply-line connection for a respective supply line. The accumulating sleeve forms a first supply-line portion, is designed for insertion into a respective shaft of the respective inflow and outflow apparatus and is dimensioned such that, in a state in which the insert has been inserted into the respective shaft, the entry opening of the accumulating sleeve is located in the vicinity of an opening between a respective head part and the respective shaft of the respective inflow and outflow apparatus. Furthermore, the
(Continued)

accumulating sleeve is connected to the supply-line connection for a respective supply line via the entry line, which constitutes a second supply-line portion.

14 Claims, 4 Drawing Sheets

(51) Int. Cl.
*G01N 21/05* (2006.01)
*G01N 21/27* (2006.01)

(52) U.S. Cl.
CPC ............... *G01N 2001/2279* (2013.01); *G01N 2001/2285* (2013.01)

(58) Field of Classification Search
USPC .............. 73/29.05, 31.05, 170.02, 756
See application file for complete search history.

(56) References Cited

U.S. PATENT DOCUMENTS

| | | |
|---|---|---|
| 7,357,572 B2 | 4/2008 | Benning et al. |
| 7,828,477 B2 | 11/2010 | Benning et al. |
| 8,104,955 B2 | 1/2012 | Benning et al. |
| 2004/0177683 A1* | 9/2004 | Ice .................... G01K 13/02 73/170.02 |
| 2006/0050767 A1* | 3/2006 | Fleming .................. G01K 1/14 374/141 |
| 2009/0003408 A1* | 1/2009 | Severson ............... B64D 15/20 374/16 |
| 2014/0169401 A1* | 6/2014 | Schwie ................ G01K 13/028 374/100 |

FOREIGN PATENT DOCUMENTS

| | | |
|---|---|---|
| CN | 103038646 A | 4/2013 |
| CN | 103884452 A | 6/2014 |
| DE | 41 00 363 A1 | 7/1992 |
| EP | 0 523 396 A1 | 1/1993 |
| EP | 1 457 765 A1 | 9/2004 |
| EP | 1 615 028 A1 | 1/2006 |
| EP | 2 700 925 A2 | 2/2014 |
| WO | 2008/058872 A2 | 5/2008 |

OTHER PUBLICATIONS

C.A.M. Brenninkmeijer, et al; "CARIBIC—Civil Aircraft for Global Measurement of Trace Gases and Aerosols in the Tropopause Region"; Journal of Atmospheric and Oceanic Technology; vol. 16; Oct. 1999; pp. 1373-1383.
C.A.M. Brenninkmeijer, et al; "Civil Aircraft for the regular investigation of the atmosphere based on an instrumented container: The new CARIBIC system"; Atmospheric Chemistry and Physics; Bd. 7, No. 18; Sep. 27, 2007; pp. 4953-4976.

* cited by examiner

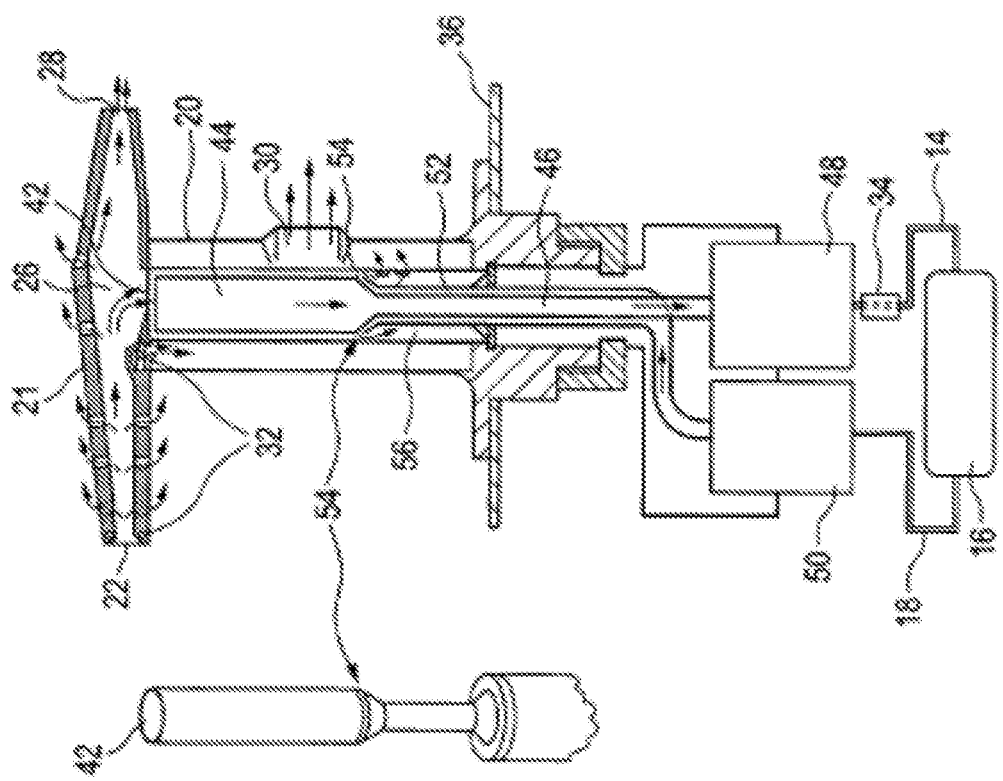

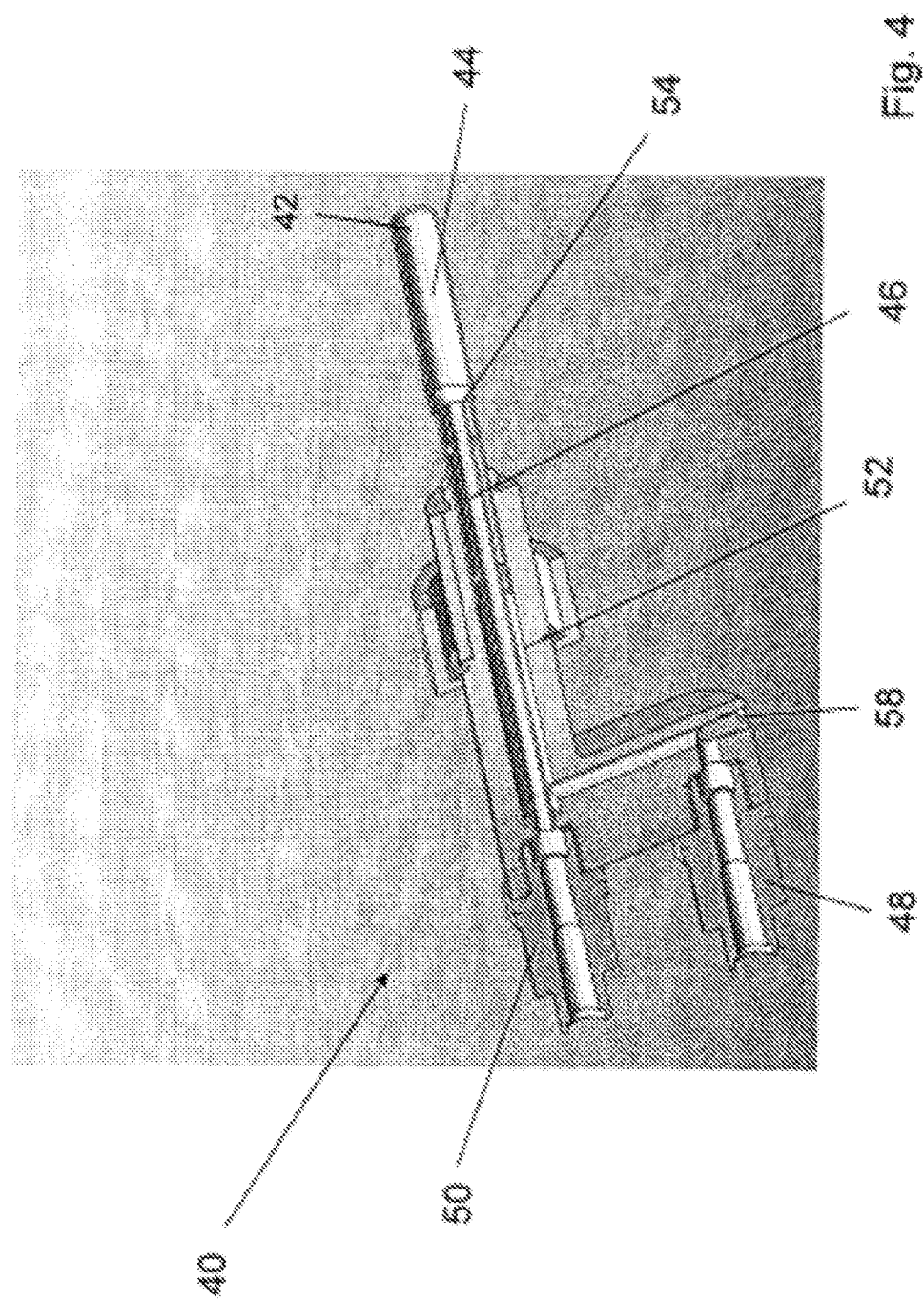

INSERT FOR AN INFLOW AND OUTFLOW APPARATUS

CROSS REFERENCE TO RELATED APPLICATIONS

This application is the U.S. National Stage of International Application Number PCT/EP2015/077573 filed on Nov. 24, 2015, which application claims priority under 35 USC § 119 to European Patent Application No. 14194585.7 filed on Nov. 24, 2014. Both applications are hereby incorporated by reference in their entirety.

TECHNICAL FIELD

The invention relates to an insert for an inflow and outflow apparatus, to an inflow and outflow apparatus for air for supplying air to be measured, to a system for determining the water vapor content or other gaseous constituents of the ambient air of an aircraft in flight, and to a water vapor measuring installation.

BACKGROUND OF THE INVENTION

In the description hereunder, reference is made in this invention predominantly to "water vapor" gas. The insert is provided for insertion into a respective inflow and outflow apparatus. Inflow and outflow apparatuses can be employed in the application for measuring humidity, for example. Water vapor measuring installations for aircraft are known in principle and typically have an inflow and outflow apparatus (measuring probe) which serves for receiving air from the environment of an airplane and to dispense said air back to said environment. The air that is received by the inflow and outflow apparatus is supplied to the actual measuring system by way of a supply line, the determination of the water vapor content of the air then being performed in said measuring system. The measuring system that is referred to here has a measuring chamber and is accommodated within the airplane. In the operation of the airplane, air permanently flows through the inflow and outflow apparatus and by way of the supply line into and through the measuring system having the measuring chamber, and subsequently by way of the discharge line back to the inflow and outflow apparatus, and from there is dispensed back into the environment of the airplane. The air that flows through the measuring system is also referred to as measured air.

SUMMARY OF THE INVENTION

It is an objective of the invention to provide an improved insert for an inflow and outflow apparatus for air for supplying air to be measured to a water vapor measuring installation.

According to the invention, this objective is achieved by an insert for an inflow and outflow apparatus that is mountable on an aircraft, having an accumulator sleeve, an inflow line, and at least one exit opening. The accumulator sleeve has an entry opening. The inflow line has a supply line connector for a respective supply line, for example to a water vapor measuring installation. The accumulator sleeve forms a first supply line portion of such a supply line. The accumulator sleeve is configured for insertion into a hollow shaft of the respective inflow and outflow apparatus, and is dimensioned such that when the insert is inserted into the shaft the entry opening is located close to an opening between a respective head part and the respective shaft of the respective inflow and outflow device. Furthermore, the accumulator sleeve by way of the inflow line as a second supply line portion is connected to the supply line connector for a respective supply line. The accumulator sleeve is furthermore configured such that it generates a pressure differential between the entry opening of the accumulator sleeve and the at least one exit opening of the insert, when the insert is inserted into the shaft. The pressure differential ensures that air flows from the head part of the inflow and outflow apparatus through the insert to a measuring apparatus that is connected to said inflow and outflow apparatus, and from the measuring apparatus back to the exit opening of the insert.

The insert, in particular the accumulator sleeve, is thus designed in such a manner that said insert can be inserted into and used in a respective shaft of a respective inflow and outflow apparatus that is mountable on an aircraft. The respective inflow and outflow apparatus has an air inflow, a hollow head part, a hollow shaft, and a fastening portion. The air inflow of the respective inflow and outflow apparatus is connectable to that inflow line of the insert that has the supply line connector for the respective supply line. The respective supply line is preferably a line to a respective measuring chamber of a respective measuring system which in operation is located in the interior of a respective aircraft.

The shaft of the respective inflow and outflow apparatus extends between the fastening portion and the head part and encloses the inflow line of the insert. The fastening portion of the respective inflow and outflow apparatus is configured for fastening the respective inflow and outflow apparatus to a respective aircraft. The air inflow of the respective inflow and outflow apparatus preferably has such a spacing from the fastening portion so that the air inflow is outside a friction layer (barrier layer) about a surface of the respective aircraft, when the respective inflow and outflow apparatus is mounted on the respective aircraft in flight. The length and shape of the insert is thus defined by the parameters which are predefined by the inflow and outflow apparatus. The insert is particularly preferably provided for the use in an inflow and outflow apparatus having a housing variant of the Rosemount® 102 BX (or -BW) type. The insert can preferably also be used in inflow and outflow apparatuses of similar dimensions.

The invention furthermore relates to an inflow and outflow apparatus that is mountable on an aircraft, having an air inflow and an air outlet, and a fastening portion for fastening the inflow and outflow apparatus to an aircraft. The air inflow has such a spacing from the fastening portion that the air inflow is outside a friction layer (barrier layer) about a surface of an aircraft, when the inflow and outflow apparatus is mounted on a aircraft in flight. The air inflow is furthermore connected to an inflow line which has a supply line connector for a supply line, so as to guide air that enters the air inflow to a measuring chamber of a measuring system which in operation is located in the interior of an aircraft. The air outlet is furthermore connected to a discharge connector for a discharge line for guiding air that exits the measuring chamber to the air outlet of the inflow and outflow apparatus.

The invention thus also relates in particular to an inflow and outflow apparatus that is mountable on an aircraft, having an insert that is inserted into the inflow and outflow apparatus. The inflow and outflow apparatus that is mountable on an aircraft comprises an air inflow, a head part, a shaft, and a fastening portion. The air inflow is connected to that inflow line of the insert that has the supply line connector for the supply line. The shaft extends between the fastening portion and the head part, and encloses the inflow line of the insert. The fastening portion is configured for fastening the inflow and outflow apparatus to an aircraft. The air inflow preferably has such a spacing from the fastening portion that the air inflow is outside a friction layer (barrier layer) about a surface of an aircraft, when the inflow and outflow apparatus is mounted on an aircraft in flight.

In one preferred design embodiment of the inflow and outflow apparatus that is mountable on an aircraft, having an insert that is inserted into the inflow and outflow apparatus, the head part has the air inflow on a front end. The head part furthermore encloses a flow duct that is open on both sides, the forward open end of which being the air inflow, and which flow duct in operation is perfused by air and is disposed such that said flow duct in operation runs almost parallel with the flow bearing thereon. The rearward open end of the flow duct has a smaller cross section than the air inflow. The inflow and outflow apparatus furthermore has a probe heater. The probe heater is disposed on an end face of the inflow and outflow apparatus, or between the air inflow and the inflow line. The probe heater can for example be disposed on the transition, or close to the transition, between the air inflow and the accumulator sleeve. The inflow and outflow apparatus can also have a plurality of probe heaters which in this case are preferably disposed on an end face of the inflow and outflow apparatus, and between the air inflow and the inflow line, for example on the transition, or close to the transition, between the air inflow and the accumulator sleeve.

The invention furthermore relates to a water vapor measuring installation, having an inflow and outflow apparatus that is mountable on an aircraft, having an insert that is inserted into the inflow and outflow apparatus, and a supply line, a measuring system having a measuring chamber, and a discharge line. The supply line is tightly connectable to the supply line connector of the insert, or of the inflow and outflow apparatus, respectively, and to an entry of the measuring chamber. The discharge line is connectable to an exit of the measuring chamber and to a discharge line connector of the insert, or of the inflow and outflow apparatus, respectively. The measuring system is configured for determining the water vapor content of air in the measuring chamber.

The inventors have recognized that it is advantageous for a pressure differential between the entry opening of the accumulator sleeve and the exit opening of the insert to build up during the in-flight operation of an aircraft, said pressure differential causing the perfusion of air, in particular measured air. The entry opening of the accumulator sleeve is connected to the air inflow, and the exit opening of the insert is connected to the air outflow. A pressure differential between the air inlet and the air outlet thus builds up during the in-flight operation of an aircraft, said pressure differential causing the perfusion of air. A pump for suctioning and/or pumping the air is not required by virtue of the pressure differential. A further aspect of the invention that has been recognized by the inventors is that an accumulation effect which causes adiabatic heating of the measured air arises at a measured-air inflow that is aligned so as to be counter to the incoming flow. The adiabatic accumulation effect and a probe heater that in a preferred design embodiment is disposed on the inflow and outflow apparatus thus enables an increase in the temperature of the measured air such that the temperature of the measured air is not close to the respective dew point. On account thereof, the risk of any condensate formation which would compromise a measurement of water vapor, that is to say the determination of the water vapor content of the measured air, can be reduced. This is the consequence of the temperature of the measured air and thus also the dew point differential of the measured air being elevated. Heating of the measuring chamber can thus be dispensed with. Furthermore, contact with particles that are deposited on the aircraft external skin can be reduced by spacing the entry opening apart from the aircraft surface. Potential mixing of the measured air that enters the measuring system with air that exits the pressurized cabin can furthermore be prevented. The inflow and outflow apparatus furthermore enables the density of the water vapor to be measured to be increased, on account of which a reduction of the lower reaction threshold of the measuring system can take place. The inflow and outflow apparatus can prevent that supercooled water particles are deposited on the end face of the entry opening of the inflow and outflow apparatus that is exposed to the flow of the aircraft and thus pose a risk to air safety. Any inhomogeneities in the density of the measured gas can be avoided since the measuring chamber in the measuring system optionally no longer has to be heated because of a potential risk of condensation that would otherwise be present.

The inflow and outflow apparatus should preferably be disposed within 3 m to 5 m behind the fuselage nose of the airplane, that is to say having the entry opening outside the turbulent friction layer (barrier layer) which is located about the airplane. The friction layer about the airplane is the fluid-dynamic barrier layer of the air that flows around the aircraft and as a result of the friction on an aircraft surface has a velocity that is less than that of more remote air. An exchange in terms of impulses, heat, molecules or particles, respectively, with the wall face of the airplane takes place within the friction layer. Since the air inflow of the inflow and outflow apparatus and therefore in the state in which the insert is inserted into the shaft of the inflow and outflow apparatus also the entry opening of the accumulator sleeve of the insert is disposed outside the friction layer, the measured air that enters in the inflow and outflow apparatus is not subject to any influence by way of properties of the wall face, such as of wetting by water or an upstream leakage of the pressurized cabin, for example.

As a consequence of the spacing provided according to the invention of the air inflow from the external surface of the airplane, the air in operation of the airplane impacts the air inflow at that relative velocity that corresponds approximately to the velocity of the airplane relative to the air, that is to say to the air speed. In operation, the ambient air that impacts the air inflow is decelerated relative to the airplane and, on account thereof, is compressed such that said air, caused by the accumulation effect, is heated in an adiabatic manner. Heating herein depends on the impact pressure prevailing on the air inflow, said impact pressure in turn depending on the velocity. As a result, the measured air is warmer than the ambient air such that the risk of any condensate formation is reduced. On account thereof, further heating of the measured air can be largely dispensed with, in particular in the measuring chamber.

In one preferred design embodiment, the inflow line that serves as the second supply line portion has a reduced diameter in relation to the accumulator sleeve that serves as the first supply line portion, on account of which in the state in which the insert is inserted into the respective shaft the pressure differential between the entry opening of the accumulator sleeve and the at least one exit opening of the insert is generated. In the state in which the insert is inserted into the respective shaft, an internal cavity is formed between the external wall of the insert and the internal wall of the shaft.

Air flows inter alia past the first supply line portion having the enlarged diameter, and therein, by virtue of a constriction as a result of a comparatively minor spacing between the external wall of the first supply line portion and the internal wall of the shaft, is accelerated such that a static pressure that is lower than on the entry opening of the accumulator sleeve results on the exit opening of the insert.

When the insert is inserted into the respective shaft, the insert is preferably configured for connecting the respective inflow and outflow apparatus by way of the respective supply line and a respective discharge line to a respective measuring chamber of a respective measuring system which in operation is located in the interior of a respective aircraft. The measuring system preferably serves for measuring water vapor. The at least one exit opening is particularly preferably connectable to the respective discharge line, and is configured for discharging a fluid, for example air, and in particular measured air, from the insert, when the insert is inserted into the respective shaft. The insert is preferably connectable to the respective discharge line in such a manner that the insert can guide air that exits the respective measuring chamber to a respective air outlet of the respective inflow and outflow apparatus that is mountable on an aircraft.

In one further preferred design embodiment, the insert can alternatively or additionally be configured in such a manner that said insert can be inserted into the respective inflow and outflow apparatus that is mountable on an aircraft and be removed therefrom again. To this end, the insert preferably has means for releasably connecting the insert to the respective shaft of the respective inflow and outflow apparatus. In particular, means can be holding elements, clamping elements, fastening elements, anchoring elements, or the like, such as, for example, screws, hooks, clamps, holders, rivets, screws, bolts, or the like. Union nuts preferably serve as means for releasably connecting the insert to the respective shaft of the respective inflow and outflow apparatus.

The insert preferably has a discharge line connector for a respective discharge line. The insert furthermore preferably has an outflow jacket tube that surrounds the inflow line and is connected to the discharge line connector for the respective discharge line. The outflow jacket tube particularly preferably has the at least one exit opening. The at least one exit opening can be disposed on or close to the transition between the first supply line portion and the second supply line portion. Furthermore, the at least one exit opening is preferably configured for discharging a fluid from the outflow jacket tube. The first supply line portion preferably has a cross section that is larger than the sum of the cross sections of the second supply line portion and of the outflow jacket tube that surrounds the second supply line portion.

The at least one exit opening can be an exit slot, for example, which is configured for discharging a fluid from the insert.

In one preferred design embodiment, the insert has a set screw which is configured for causing an adjustable constriction by way of which a quantity of air from the point of entry and thus the pressure in the air guiding system are capable of being set. The set screw is preferably disposed within the inflow line. The set screw is particularly preferably disposed on the transition, or close to the transition, between the inflow line and the supply line connector. The quantity of air which by way of the entry opening of the accumulator sleeve enters the inflow line can thus be regulated with the aid of the set screw.

In one particularly preferred design embodiment of the insert according to the invention, the inflow line that serves as the second supply line portion has a reduced diameter in relation to the accumulator sleeve that serves as the first supply line portion, on account of which in the state in which the insert is inserted into the respective shaft the pressure differential between the entry opening of the accumulator sleeve and the at least one exit opening of the insert is generated. The insert is furthermore configured for connecting the respective inflow and outflow apparatus by way of the respective supply line and a respective discharge line to a respective measuring chamber of a respective measuring system which in operation is located in the interior of a respective aircraft, when the insert is inserted into the respective shaft. Furthermore, the insert is connectable to the respective discharge line in such a manner that the insert can guide air that exits from the respective measuring chamber to a respective air outlet of the respective inflow and outflow apparatus that is mountable on an aircraft. The insert furthermore has a discharge line connector for the respective discharge line, and the insert has an outflow jacket tube that surrounds the inflow line and is connected to the discharge line connector for the respective discharge line. The outflow jacket tube furthermore has the at least one exit opening, and the at least one exit opening is disposed on or close to the transition between the first supply line portion and the second supply line portion, and is configured for discharging a fluid from the outflow jacket tube. Furthermore, the first supply line portion has a cross section that is larger than the sum of the cross sections of the second supply line portion and of the outflow jacket tube that surrounds the second supply line portion.

The combination of the aforementioned features enable the implementation of various advantages. In particular, this particularly preferred design embodiment enables the use of the insert in an inflow and outflow apparatus without additional pumps, since the air by way of an air inflow is suctioned into the entry opening of the insert and is suctioned out at the exit opening, in order to then be guided out through the air outlet of the respective inflow and outflow apparatus. Therefore, in the state in which the insert is inserted into the respective inflow and outflow apparatus, said insert continuously supplies a measuring system, in particular for measuring water vapor, with air. The insert enables a flow velocity of the air of between 3 and 5 liters per minute, for example, that is required for the measurement to be achieved without the additional use of pumps. Furthermore, the air can be provided in the respective measuring chamber of the respective measuring system at a temperature such that heating of the measuring chamber is not necessary. Heating of the measuring chamber could cause an inhomogeneous distribution of the temperature during the measuring and thus increase the measuring error.

The inflow and outflow apparatus according to the invention is hereunder also referred to as a Ram Air Intake for Water Vapor Measurement (RAIWaM)

For the sake of simplicity, the acronym RAIWaM will be used hereunder.

The external jacket part of the RAIWaM can be an overall temperature measurement housing that is customary for airplanes and which hereunder will also be referred to as a TAT housing (TAT=Total Air Temperature), such as has been used to date for measuring air temperature. However, conventional housings of this type for measuring air temperature do not have an supply line and discharge line and consequently also no supply line and discharge line connectors for connecting to a measuring system for determining the water vapor content of the air. The aerodynamic and thermodynamic principle of operation of the TAT housings is discussed in Stickney et al. (1994); c.f. STICKNEY, T. M.; SHEDLOV, M. W., THOMPSON, D. I., 1994: Goodrich Total Temperature Sensors, Goodrich Corporation, Burnsville, Me., USA. One potential housing variant is that of the Rosemount® 102 BX (or -BW) type, which has a removable temperature measurement element.

The accumulation-related adiabatic heating of the measured air at Mach 0.85 and at an altitude of 200 hPa is approx. 30 K. Even at lower velocities and at lower altitudes, adiabatic heating ensures that the air temperature is always sufficiently spaced apart from the potential dew point. The only exception exists when flying through clouds, which can in the retrospective conversion of the water vapor mixture ratio into relative humidity potentially lead to a value in excess of 100%. Ultimately, this value can also be used as an indicator for the presence of liquid or solid water particles, that is to say clouds or precipitation.

In one potential design embodiment of the inflow and outflow apparatus that is mountable on an aircraft, the spacing between the fastening portion and the air inflow is between 50 mm and 150 mm, in particular between 80 mm and 100 mm. The inflow and outflow apparatus that is mountable on an aircraft can have a spacing between the fastening portion and the air inflow of 87 mm, for example.

In one preferred design embodiment of the inflow and outflow apparatus according to the invention, the inflow and outflow apparatus has a head part, a shaft, and a flange. The shaft extends between the flange and the head part, and encloses the inflow line. The head part has the air inflow on a front end. The flange forms the fastening portion for fastening the inflow and outflow apparatus to an aircraft. Furthermore, the head part can enclose a flow duct that is open on both sides, the forward open end of which being the air inflow, and which flow duct in operation is perfused by air and is disposed such that said flow duct in operation runs almost parallel with the flow bearing thereon. Furthermore, the flow duct, in terms of the internal cross section downstream of the air inflow, can initially widen and subsequently taper off toward the open rearward end of said flow duct that forms an air outflow. The supply line can branch off from a portion of the flow duct that is widened in the internal cross section. Moreover, the rearward open end of the flow duct can have a smaller cross section than the air inflow. The smaller cross section at the rearward open end of the flow duct generates a flow constriction which in the inflight state of the airplane generates the increase in pressure that is created at the point of entry to the comparatively velocity-reduced section, and thus creates the adiabatic heating of the measured air. The sum of the impact force and of the static pressure, that is to say the total pressure and thus also the adiabatic heating effect, is maintained along the flow duct or in the entire measured section up to the point of flow constriction.

In one design embodiment, the inflow and outflow apparatus that is mountable on an aircraft has a probe heater. The probe heater is preferably disposed on an end face of the inflow and outflow apparatus, and/or on the transition, or close to the transition, between the air inflow and the inflow line.

The inflow and outflow apparatus that is mountable on an aircraft preferably has a heated entry opening. The probe heater that is preferably provided to this end serves for avoiding the formation of ice and is preferably disposed on the end face of the inflow and outflow apparatus.

Additionally or alternatively, the inflow and outflow apparatus that is mountable on an aircraft can have a heater that is disposed on the supply line to the measuring chamber. The heater that is disposed on the supply line serves for heating the measured air before the latter enters the actual measuring process in the measuring chamber, and thus renders heating of the measured air in the measuring chamber superfluous. It is possible that the adiabatic heating of the measured air that is caused by the accumulation effect is still considered to be insufficient for reliably preventing condensate formation. In this case, the heater can serve for heating the inflow line between the RAIWaM and the measuring system, in order for the measured air to thus be heated. Accordingly, it can be provided according to one preferred variant of embodiment that the supply line to the measuring chamber has a heater for heating air that flows through the supply line. In that the heater is disposed in the region of the supply line, it is possible for the measured air to be sufficiently heated before entering the measuring chamber, such that the measured air does not have to be heated within the measuring chamber and thus has a homogeneous temperature.

The measuring chamber of the measuring system is preferably an absorptiometric measuring chamber which allows the water vapor content to be determined by means of absorptiometric spectrometry, for example.

In one exemplary application case of the RAIWaM for the measuring system type WVSS-II of SpectraSensors Inc., USA, said RAIWaM has a measuring chamber for determining the water vapor content by means of absorptiometric spectrometry. Absorptiometric spectrometry is a method for determining the water vapor content of air. A column of measured air is penetrated by a measuring light beam, the absorption of said light beam at a specific wave length representing the measure of the water vapor density. In order for an air humidity parameter that is conservative in physical terms, such as the mixing ratio of the water vapor mass, for example, to be calculated, apart from the water vapor density, measuring the pressure and the temperature of the contents of the chamber is also required. The latter variable can only be performed at a finite number of measuring points within the chamber. A homogeneous temperature field is required for this reason, in order for a representative temperature value to be obtained. This objective and a direct heating of the chamber would be mutually conflicting. The adiabatic heating effect of the RAIWaM is a significant step in order for the described objective to the achieved.

The benefits that are achieved or are achievable, respectively, by way of the inflow and outflow apparatus and the potential design embodiments thereof are as follows:
  internal condensation in the equipment can be avoided or at least reduced without dedicated heating of the core parts of the measuring system, thus of the absorptiometric or scatter measuring chamber in the case of an optical method;
  since the air entry of the RAIWaM in the case of an aerodynamically correct positioning lies on the aircraft fuselage, outside the friction layer,
  cabin leakages in the region of the incoming flow cannot generate any disturbances;
  water or ice deposits in the region of the incoming flow on the external skin of the airplane can remain without influence (no memory effects);
  because of the accumulation effect, a water vapor density that is significantly increased in relation to the ambient air (by up to 50%) can have the end effect of ensuring that reaction threshold of the measuring method is lowered.

In order for the specified properties (air entry point outside the barrier layer of the aircraft body) to be present, the air inflow of the RAIWaM should be accommodated at the same spacing from the aircraft nose or the fuselage nose, respectively, as also has to be adhered to for the temperature sensors of the aircraft.

The invention furthermore relates to a water vapor measuring installation, having an inflow and outflow apparatus and a supply line, a measuring system having a measuring chamber and a discharge line. The supply line is tightly connected to the supply line connector of the inflow and outflow apparatus and to an entry of the measuring chamber. The discharge line is connected to an exit of the measuring chamber and to a discharge line connector of the inflow and outflow apparatus. The measuring system is configured for determining the water vapor content of air in the measuring chamber.

In one preferred design embodiment of the water vapor measuring installation, the measuring chamber is an absorptiometric measuring chamber which allows the air humidity to be determined by means of an absorptiometric spectrogram.

The invention includes the finding that known water vapor measuring installations have the following disadvantages:

The air that flows into the air inflow has previously been in contact with the upstream fuselage surface. Depending on the wetting of the latter by water or ice, and on the temperature, inertia effects (also referred to memory effects) that are not reproducible can be created.

Due to small leaks in the upstream part of the pressurized cabin that arise on occasion, the measuring air can be contaminated by the interior air of the cabin that is enriched with water vapor. The leaks can be created in the course of aging of the aircraft on doors, windows, flaps, plug connectors, landing gear wells and on all transitions of components of the fuselage, for example by symptoms of fatigue on the butt seams of the aluminum panels. These leaks are insignificant in terms of the in-flight operation, but are fatal in terms of water vapor measurement. The effect is enhanced at increasing altitude, that is to say as the pressure differential between the cabin and the environment increases. The effect is predominantly dependent on the type and age of the aircraft. However, individual differences can arise in the case of aircraft of identical type. As a matter of principle, there is no capability of calibrating these error effects which are possible at all times.

The design objective underlying the earlier inflow and outflow apparatus, the so-called "Air Sampler" (part of the WVSS-II system by SpectraSensors Inc., USA), specifically maintaining the ambient pressure of the aircraft (static pressure), has proven to be a disadvantage. In the case of a relative humidity of the ambient air of close to 100%, condensation which can be disturbing to the measuring process in a decisive manner can arise in the internal part of the measured air path (hoses, transition pieces, and absorption chamber). There are two reasons for this:

The Air Sampler can be accommodated at a location of the aircraft that is subject to negative pressure caused by the circulating flow. Even just the adiabatic cooling that is directly associated therewith rapidly reaches the dew point in the case of comparatively high levels of humidity.

In the case of a descent, that is to say in the transition from comparatively cool to comparatively warm conditions, thermal inertia of the internal walls of the entry air routing and of the absorptiometric chamber causes the dew point to be undershot.

The two last-mentioned effects often cause an undesirable condensate formation within the measured air lines and above all within the absorptiometric measuring chamber.

It is advantageous for the TAT housing of the RAIWaM to be heatable (approx. 300 W) in order for the risk of the formation of ice on the probe that puts the aircraft at risk to be eliminated in this way.

The RAIWaM according to one preferred variant of embodiment has a TAT housing, the temperature measuring element of the latter being replaced by a specially made insert, that is to say the insert according to the invention. The aerodynamic and thermodynamic conditions are described by Stickney et al. (1994). The invention therefore also relates to the insert for a respective inflow and outflow apparatus. The insert has a accumulator sleeve as the first supply line portion, said insert being configured for insertion into the shaft of the inflow and outflow apparatus, and being dimensioned such that an entry opening of the accumulator sleeve is located close to the opening between the head part and the shaft of the inflow and outflow apparatus. The accumulator sleeve by way of an inflow line as the second supply line portion is connected to a supply line connector for the supply line.

The insert preferably has an outflow jacket tube that surrounds the inflow line and is connected to a discharge line connector for the discharge line. The insert furthermore has means for releasably connecting the insert to the shaft of the inflow and outflow apparatus. Means for releasably connecting the insert to the shaft of the inflow and outflow apparatus can be clamping elements or fastening elements, such as clamps, screws, or the like, for example. The outflow jacket tube can furthermore have exit openings or slots which are disposed on or close to the transition between the first supply line portion and the second supply line portion and which are configured for discharging a fluid, for example the measured air, from the outflow jacket tube. In one preferred design embodiment of the insert, the first supply line portion has a cross section that is larger than the sum of the cross sections of the second supply line portion and of the outflow jacket tube that surrounds the second supply line portion. In the state in which the insert is inserted into the shaft of the inflow and outflow apparatus, a space about the outflow jacket tube that facilitates discharging of the air from the exit slots is thus generated.

The invention furthermore relates to the use of an insert according to the invention in an inflow and outflow apparatus that is mountable on an aircraft. The inflow and outflow apparatus that is mountable on an aircraft has an air inflow, a head part, a shaft, and a fastening portion. The air inflow is connected to the inflow line of the insert which has the supply line connector for the respective supply line. The shaft extends between the fastening portion and the head part, and encloses the inflow line. The fastening portion is configured for fastening the inflow and outflow apparatus to an aircraft. The air inflow preferably has such a spacing from the fastening portion that the air inflow is outside a friction layer (barrier layer) about a surface of an aircraft, when the inflow and outflow apparatus is mounted on a aircraft in flight.

BRIEF DESCRIPTION OF THE DRAWINGS

The invention is now to be explained in more detail with reference to an exemplary embodiment by means of the figures, in which

FIG. 3a: shows a sectional illustration of the principle diagram of the inflow and outflow apparatus, for explaining the operation of the RAIWaM;

FIG. 3b: shows a perspective fragmented view of an insert; and

FIG. 4: shows a partially sectional perspective view of the insert in the inflow and outflow apparatus as the RAIWaM, for connecting the inflow and outflow apparatus to a measuring system that is disposed in the interior of the aircraft.

DETAILED DESCRIPTION

Figure 1:
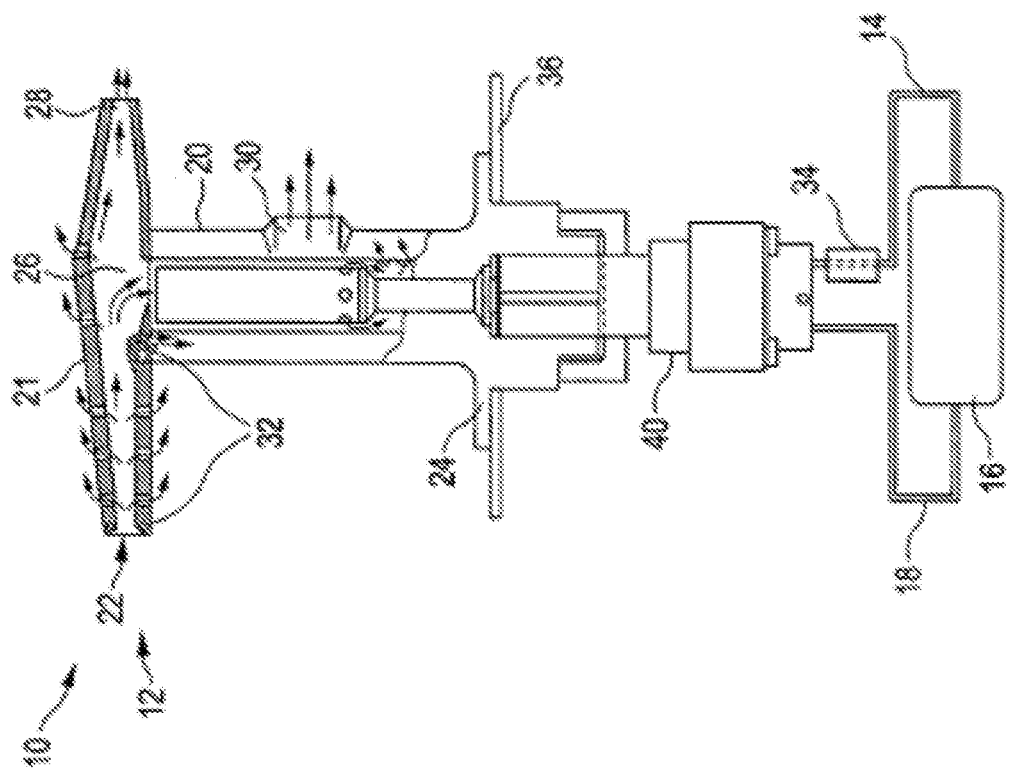
FIG. 1: shows a schematic view of a water vapor measuring installation having an inflow and outflow apparatus for air having an insert for connecting to a water vapor measuring system.

FIG. 1 shows a view of a water vapor measuring installation 10, having an inflow and outflow apparatus 12 that serves as a Ram Air Intake for Water Vapor Measurement (RAIWaM), having a shaft 20 that serves as an outrigger. An insert 40 is inserted into the inflow and outflow apparatus 12, by means of which the inflow and outflow apparatus 12 by way of a supply line 14 and a discharge line 18 is connected to a measuring chamber 16 of a measuring system. The insert 40 is removable.

The water vapor measuring installation 10 thus has a measuring probe 12 as the RAIWaM in the form of a TAT housing (TAT=Total Air Temperature). Moreover, the water vapor measuring installation 10 has a first air routing as the supply line 14, a measuring chamber 16 having the actual water vapor measuring system, and a second air routing as the discharge line 18, said elements in operation being sequentially perfused by measured air. The supply line 14 extends from the insert 40, or from the TAT housing 12 (measuring probe 12), respectively, to a measuring chamber entrance of the measuring chamber 16. The discharge line 18 extends from a measuring chamber exit of the measuring chamber 16 back to the insert 40, or to the TAT housing 12, respectively.

The TAT housing 12 has a shaft 20 as an outrigger, an aerodynamically shaped head part 21 having an air entry or air inflow 22 being provided at the one end of said shaft 20, and a fastening end in the form of a flange 24 for fastening to an airplane being provided at the other end of said shaft 20.

The shaft 20 is dimensioned such that the air inflow 22 as the air entry is in the region of the first few meters behind the aircraft nose, so as in the inflight operation to be outside a fluid-dynamic barrier layer around the airplane that is in the in-flight state, and to which the inflow and outflow apparatus 12 is fastened.

Figure 2:
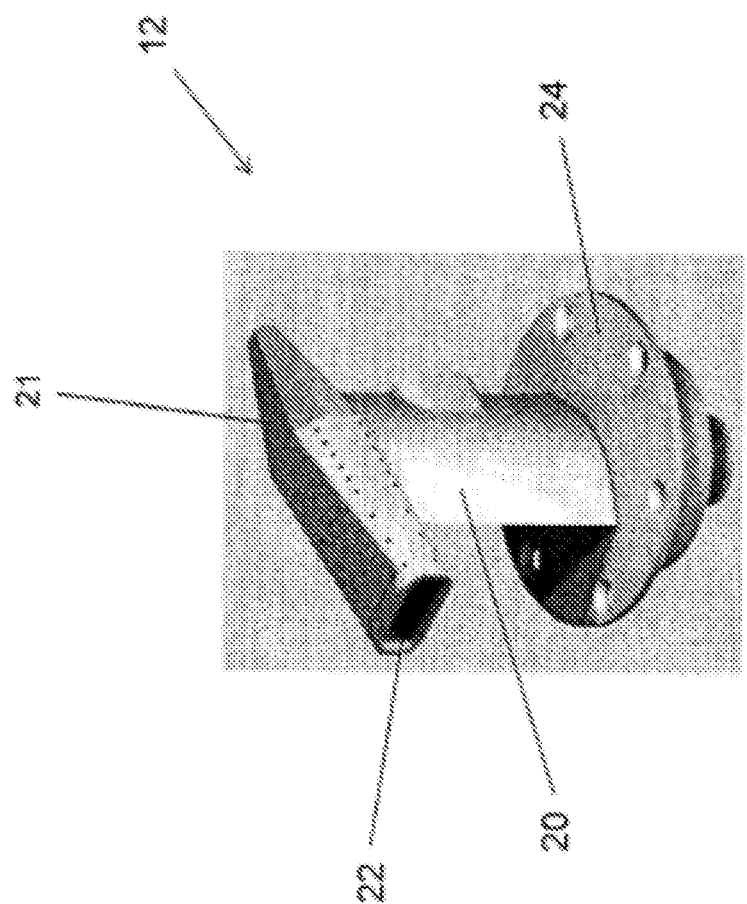
FIG. 2: shows a perspective external view of the inflow and outflow apparatus.

FIG. 2 shows a perspective external view of an inflow and outflow apparatus 12 having a head part 21, a shaft 20, and a fastening portion in the form of a flange 24. The air inflow 22 which serves for supplying air is disposed on a front end of the head part 21.

FIG. 3 illustrates the internal construction and the operation of the entire measuring installation, including the RAIWaM. The head part 21 encloses a flow duct 26 that is open on both sides, the forward open end of said flow duct 26 being the air inflow 22. The rearward open end of the flow duct 26 forms an air outflow 28. The internal cross section of the flow duct 26 initially widens between the air inflow 22 and the air outflow 28, then decreases again toward the air outflow 28. The air outflow 28 has a smaller cross section that the air inflow 22.

The supply line 14 branches off from the flow duct 26 where the latter has an enlarged internal cross section. To this end, the supply line 14 by way of an inflow line 46 and an entry opening 42 of an accumulator sleeve 44 of the insert 40 is in fluid communication with the flow duct 26. The discharge line 18 is in fluid communication with an air outlet 30 which is disposed on a rear edge of the shaft 20. The discharge line 18 herein by way of an outflow jacket tube 52 and exit openings in the form of exit slots 54 is in fluid communication with the air outlet.

In relation to the shaft 20, or to the flange 24 thereof, respectively, the flow duct 26 is aligned such that the latter in operation runs so as to be approximately parallel with the direction of the incoming flow of the ambient air. Ambient air that impacts the air inflow 22 in operation accumulates at the air inflow 22, and is adiabatically heated by this accumulation effect. Accordingly, the measured air in relation to the ambient air is heated. The heated measured air flows out of the flow duct 26 by way of the entry opening 42 of the accumulator sleeve 44 and the inflow line 46 into the supply line 14, and through the latter into the measuring system having the measuring chamber 16. Water vapor measuring takes place therein by means of absorptiometric spectrometry. The measured air subsequently exits the measuring chamber 16 and the measuring chamber exit thereof, into the second air routing, or the discharge line 18, respectively, and from the latter is guided back to the discharge line connector 50 again.

The air within the head part 21 is thus deflected at a right angle to the accumulator sleeve 44, the actual inlet opening for the temperature measuring probe, or optionally an onward routing. Upstream of this deflection point the head part 21 is provided with bores which by way of the suction effect of the external circulating flow suction the friction layer of the internal flow, thereby reducing the friction layer. It is thus achieved that the deflected part of the flow upstream has largely no contact with the housing wall. The undisturbed adiabatic accumulation effect on the entry opening 42 of the accumulator sleeve 44 can thus be created in the case of the original use as a temperature measuring apparatus. The heating effect of said adiabatic accumulation effect on the sensor that is located in the sleeve is compensated for by a simple computing method. The accumulation effect is achieved by narrow exit openings in the form of exit slots 54 on the flow-relevant end of the accumulator sleeve 44, where relative negative pressure due to aerodynamic circumstances prevails on the external side of the sleeve. The air speed at the external extremity is reduced from up to 300 m/s to a few m/s. The almost complete total pressure as the sum of the static (ambient) pressure and the impact pressure is thus achieved.

The end faces of the entry openings having an electric probe heater 32 that face the flow are provided in order for the formation of ice to be avoided on the inflow and outflow apparatus 12 that serves as a measuring probe. The first supply line 14 is provided with a heater 34 for any further heating of the measured air that can optionally be required.

The shaft 20 causes a spacing of the air inflow 22 from an aircraft surface that is formed from the aircraft external skin 36, said spacing being dimensioned such that the air inflow 22 is located outside a fluid-dynamic barrier layer about the aircraft external skin 36 and is thus freely exposed to an incoming flow at a speed which corresponds to the speed of the aircraft relative to the air (air speed). The spacing is preferably between 50 mm and 150 mm, for example between 80 mm and 100 mm. The spacing is particularly preferably 87 mm.

Instead of a temperature probe that would otherwise be provided, an insert 40, which is inserted into the TAT housing 12 and is connected to both the supply line 14 and to the discharge line 18 and forms a supply line portion and a discharge line portion, and thus serves for supplying and discharging measured air to and from the measuring system having the measuring chamber 16, is provided. FIG. 3 shows the insert 40 in both a schematic illustration in the cross-sectional view of the RAIWaM (FIG. 3*a*), as well as in a perspective fragmented view (FIG. 3*b*).

The insert 40 is designed such that an entry opening 42 of the insert 40 is directly adjacent to the flow duct 26. The almost full impact pressure bears on the entry opening 42 of the insert 40. The entry opening 42 is simultaneously the entrance to the supply line 14. An upper part of the insert 40 in the figure thus forms a first supply line portion 44 in the form of an accumulator sleeve, the latter being adjoined in a straight line by a second supply line portion 46 as the inflow line of the insert 40, said second supply line portion 46 having a reduced diameter in relation to the accumulator sleeve 44 that serves as the first supply line portion and leading to a supply line connector 48 to which the further supply line 14 which finally leads to the measuring chamber 16 is connected.

The insert 40 is moreover connected to the discharge line 18 and forms a discharge line portion 52. A discharge line connector 50, which leads to that discharge line portion 52 that as a jacket tube is disposed coaxially about the second supply line portion 46 and opens into an exit opening in the form of an exit slot 54 which is located where the first supply line portion 44 having the larger diameter, that is to say the accumulator sleeve, transitions into the second supply line portion 46 (that is to say the inflow line) having the smaller diameter, is provided for connecting to the remaining discharge line 18. Outflowing measured air exits from the exit slot 54 into an internal cavity 56 of the shaft 20, said internal cavity 56 in turn being in fluid communication with the air outlet 30 on the shaft 20. The internal cavity 56 is moreover in fluid communication with the flow duct 26 and is perfused by air entering the air inflow 22. Said air flows past inter alia the outside of the first supply line portion 44 having an enlarged diameter, and there, by virtue of a constriction as a result of a relatively minor spacing between an external wall of the first supply line portion 44 and an internal wall of the internal cavity 56, is accelerated such that a static pressure results that is lower in relation to the static pressure prevailing in the discharge line portion 52.

The insert 40 is designed such that the entry or accumulator sleeve 44 thereof in terms of geometry is identical to a temperature measurement insert that is used in TAT housings. The air entering runs into an inflow line 46 that is central on the axis of symmetry and leads directly to the connector piece, that is to say to the supply line connector 48 of the measured air supply line, or the supply line 14 of the actual measuring system, respectively.

The returning measured air is guided from the connector piece of the measuring system outflow, that is to say the discharge line connector 50, by way of the jacket tube 52 about the inflow line 46 to the exit slot 54 which on the insert 40 is precisely at the location where the exit openings are located on the geometrically and aerodynamically identical temperature measurement insert of the TAT housing. The air exiting from the exit slot 54 runs by way of the internal cavity 56 to the rearward exit opening which forms the air outlet 30. The pressure differential between the entry opening 42 at the front end of the accumulator sleeve 44 and the exit slot 54 ensures the flow of the measured air. A flow speed between 3 and 5 liters per minute, verified in the laboratory, ultimately results. This is more than sufficient for usual measuring systems. A dedicated pump operation is not required.

The quantity of air, and thus also the pressure in the air guiding system, from the point of entry are capable of being set by way of a set screw 58 (see sectional image in FIG. 4). The set screw 58 causes an adjustable constriction. This constriction ensures that the impact pressure is maintained in the entire measuring system. The throughput rate can be adapted to the requirements of the measuring process.

FIG. 4 shows a partially sectional perspective view of the insert 40. The entire insert 40 is insertable into the TAT housing 12 of the RAIWaM and removable therefrom.

The insert 40 is configured for being inserted into an inflow and outflow apparatus 12 that is mountable on an aircraft.

The insert 40 comprises an accumulator sleeve 44, an inflow line 46, a supply line connector 48, a discharge line connector 50, and an outflow jacket tube 52.

The accumulator sleeve 44 has an entry opening 42 and forms a first supply line portion which serves for guiding air into the inflow line 46. The accumulator sleeve 44 is configured for insertion into a respective shaft 20 of the respective inflow and outflow apparatus 12, and is dimensioned such that in the state in which the insert 40 is inserted into the respective shaft 20 the entry opening 42 of the accumulator sleeve 44 is located close to an opening between a respective head part 21 and the respective shaft 20 of the respective inflow and outflow apparatus 12 (cf. FIG. 3*a*). The inflow line 46 forms a second supply line portion, and extends from a distal end of the accumulator sleeve 44, that is to say from the transition of the insert 40 where the diameter of the latter changes, to the supply line connector 48. The supply line connector 48 is configured for connecting the insert 40 and thus the inflow and outflow apparatus 12 to a respective supply line 14. In particular, the supply line 14 guides the air into a measuring chamber 16 of a measuring system (see FIG. 3*a*) in which properties of the air are measured. The measuring chamber 16 by way of a discharge line 18 is connectable to the discharge line connector 50 of the insert 40 (cf. FIG. 3*a*). The discharge line connector 50 is thus also configured for connecting the insert 40 and thus the inflow and outflow apparatus 12 to a respective discharge line 18. The discharge line 18 guides the air out of the measuring chamber 16 to the discharge line connector 50. The discharge line connector 50 is connected to the outflow jacket tube 52 which serves as a discharge line portion and encloses the inflow line 46. The outflow jacket tube 52 terminates at exit openings in the form of exit slots 54 which are located at the transition between the inflow line 46 and the accumulator sleeve 44, that is to say at the transition of the change in diameter. Therefore, in the state in which the insert 40 is inserted into the respective shaft 20, the accumulator sleeve 44 is configured for generating a pressure differential between the entry opening 42 of the accumulator sleeve 44 and the exit slots 54 of the insert 40, said pressure differential ensuring a flow of air.

In the state in which the insert 40 is inserted into the shaft 20 of the respective inflow and outflow apparatus 12, as is shown in FIG. 3*a*, the insert, by way of a respective supply line 14 and a respective discharge line 18, thus serves for connecting the respective inflow and outflow apparatus 12, into which the insert 40 is inserted, to a respective measuring chamber 16 of a respective measuring system which in operation is located in the interior of a respective aircraft. In particular, the insert 40 enables a measuring system to be operated without any additional pump.

In the exemplary embodiment of the insert 40 shown in FIG. 4, the insert 40 has a set screw 58 at the transition between the inflow line 46 and the supply line connector 48. The set screw 58 serves for generating a constriction. The constriction can be generated by rotating the set screw 58, on account of which the volume at the transition between the inflow line 46 and the supply line connector 48 can be reduced or increased. The quantity of air and therefore the pressure in the measuring system can thus be set with the aid of the set screw 58.

LIST OF REFERENCE SIGNS

10 Water vapor measuring installation
12 Inflow and outflow apparatus, measuring probe/TAT housing
14 Supply line
16 Measuring chamber
18 Discharge line
20 Shaft/outrigger
21 Head part
22 Air inflow/air entry
24 Fastening end/fastening portion/flange
26 Flow duct
28 Air outflow
30 Air outlet
32 Probe heater
34 Heater
36 Aircraft external skin
40 Insert
42 Entry opening
44 Accumulator sleeve, first supply line portion
46 Inflow line, second supply line portion
48 Supply line connector
50 Discharge line connector
52 Discharge line portion/jacket tube
54 Exit slot
56 Cavity
58 Set screw

What is claimed is:

1. A removable insert for an inflow and outflow apparatus that is mountable on an aircraft, comprising:
an accumulator sleeve having an entry opening;
an inflow line having a supply line connector for a respective supply line; and
at least one exit opening;
wherein the accumulator sleeve forms a first supply line portion, is configured for insertion into a respective shaft of the respective inflow and outflow apparatus, and is dimensioned such that the entry opening of the accumulator sleeve in a state in which the insert is inserted into the respective shaft is located adjacent an opening between a respective head part and the respective shaft of the respective inflow and outflow apparatus;
wherein the accumulator sleeve by way of the inflow line as a second supply line portion is connected to the supply line connector for the respective supply line; and
wherein the accumulator sleeve is configured for generating, in the state in which the insert is inserted into the respective shaft, a pressure differential between the entry opening of the accumulator sleeve and the at least one exit opening of the insert, said pressure differential providing an air flow;
wherein the inflow line that serves as the second supply line portion has a reduced diameter in relation to the accumulator sleeve that serves as the first supply line portion, on account of which, in the state in which the insert is inserted into the respective shaft, the pressure differential between the entry opening of the accumulator sleeve and the at least one exit opening of the insert is generated;
wherein the insert has a discharge line connector for a respective discharge line, and the insert has an outflow jacket tube that surrounds the inflow line and is connected to the discharge line connector for the respective discharge line, and
wherein the first supply line portion has a cross section that is larger than the sum of the cross sections of the second supply line portion and of the outflow jacket tube that surrounds the second supply line portion.

2. The insert as claimed in claim 1, wherein the insert, in the state in which the insert is inserted into the respective shaft, is configured for connecting the respective inflow and outflow apparatus by way of the respective supply line and a respective discharge line to a respective measuring chamber of a respective measuring system which in operation is located in the interior of a respective aircraft.

3. The insert as claimed in claim 2, wherein in the state in which the insert is inserted into the respective shaft, the at least one exit opening is connectable to the respective discharge line and is configured for discharging a fluid from the insert.

4. The insert as claimed in claim 2, wherein the insert is connectable to the respective discharge line in such a manner that the insert can guide air that exits from the respective measuring chamber to a respective air outlet of the respective inflow and outflow apparatus that is mountable on an aircraft.

5. The insert as claimed in claim 1, wherein the outflow jacket tube has the at least one exit opening, and
wherein the at least one exit opening is disposed on or close to the transition between the first supply line portion and the second supply line portion, and is configured for discharging a fluid from the outflow jacket tube.

6. The insert as claimed in claim 1, wherein the insert has means for releasably connecting the insert to the respective shaft of the respective inflow and outflow apparatus.

7. The insert as claimed in claim 1, wherein the insert has a set screw which is configured for causing an adjustable constriction by way of which a quantity of air from the point of entry and thus the pressure in the air guiding system are capable of being set.

8. An inflow and outflow apparatus that is mountable on an aircraft, having the insert as claimed in claim 1 that is inserted into the inflow and outflow apparatus, wherein the inflow and outflow apparatus that is mountable on an aircraft comprises
an air inflow;
a head part;
a shaft; and
a fastening portion for fastening the inflow and outflow apparatus to an aircraft;
wherein the air inflow is connected to the inflow line of the insert which has the supply line connector for the respective supply line;
wherein the shaft extends between the fastening portion and the head part and encloses the inflow line of the insert; and
wherein the air inflow has such a spacing from the fastening portion that the air inflow is outside a friction layer (barrier layer) about a surface of an aircraft, when the inflow and outflow apparatus is mounted on a aircraft in flight.

9. The inflow and outflow apparatus that is mountable on an aircraft as claimed in claim 8,
wherein the head part has the air inflow on a front end;
wherein the head part encloses a flow duct that is open on both sides, the forward open end of which being the air inflow, and which flow duct in operation is perfused by air and is disposed such that said flow duct in operation runs almost parallel with the flow bearing thereon;
wherein the rearward open end of the flow duct has a smaller cross section than the air inflow;
wherein the inflow and outflow apparatus has a probe heater; and
wherein the probe heater is disposed on an end face of the inflow and outflow apparatus and/or between the air inflow and the inflow line.

10. A water vapor measuring installation, having an inflow and outflow apparatus that is mountable on an aircraft as claimed in claim 8 and a supply line, a measuring system having a measuring chamber and a discharge line, wherein the supply line is tightly connected to the supply line connector of the insert and to an entry of the measuring chamber, and the discharge line is connected to an exit of the measuring chamber and to the discharge line connector of the insert, and wherein the measuring system is configured for determining the water vapor content of air in the measuring chamber.

11. A removable insert for an inflow and outflow apparatus that is mountable on an aircraft, comprising:
an accumulator sleeve having an entry opening;
an inflow line having a supply line connector for a respective supply line; and
at least one exit opening;
wherein the accumulator sleeve forms a first supply line portion, is configured for insertion into a respective shaft of the respective inflow and outflow apparatus, and is dimensioned such that the entry opening of the accumulator sleeve in a state in which the insert is inserted into the respective shaft is located adjacent an opening between a respective head part and the respective shaft of the respective inflow and outflow apparatus;
wherein the accumulator sleeve by way of the inflow line as a second supply line portion is connected to the supply line connector for a respective supply line; and
wherein the accumulator sleeve is configured for generating, in the state in which the insert is inserted into the respective shaft, a pressure differential between the entry opening of the accumulator sleeve and the at least one exit opening of the insert, said pressure differential providing an air flow, and
wherein the inflow line that serves as the second supply line portion has a reduced diameter in relation to the accumulator sleeve that serves as the first supply line portion, on account of which, in the state in which the insert is inserted into the respective shaft, the pressure differential between the entry opening of the accumulator sleeve and the at least one exit opening of the insert is generated;
wherein the insert, in the state in which the insert is inserted into the respective shaft, is configured for connecting the respective inflow and outflow apparatus by way of the respective supply line and a respective discharge line to a respective measuring chamber of a respective measuring system which in operation is located in the interior of a respective aircraft;
wherein the insert is connectable to the respective discharge line in such a manner that the insert can guide air that exits from the respective measuring chamber to a respective air outlet of the respective inflow and outflow apparatus that is mountable on an aircraft;
wherein the insert has a discharge line connector for a respective discharge line, and the insert has an outflow jacket tube that surrounds the inflow line and is connected to the discharge line connector for the respective discharge line;
wherein the outflow jacket tube has the at least one exit opening;
wherein the at least one exit opening is disposed on the transition between the first supply line portion and the second supply line portion, and is configured for discharging a fluid from the outflow jacket tube; and
wherein the first supply line portion has a cross-section that is larger than the sum of the cross-sections of the second supply line portion and of the outflow jacket tube that surrounds the second supply line portion.

12. An inflow and outflow apparatus that is mountable on an aircraft, having the insert as claimed in claim 11 that is inserted into the inflow and outflow apparatus, wherein the inflow and outflow apparatus that is mountable on an aircraft comprises
an air inflow; a head part;
a shaft; and
a fastening portion for fastening the inflow and outflow apparatus to an aircraft;
wherein the air inflow is connected to the inflow line of the insert which has the supply line connector for the respective supply line;
wherein the shaft extends between the fastening portion and the head part and encloses the inflow line of the insert; and
wherein the air inflow has such a spacing from the fastening portion that the air inflow is outside a friction layer (barrier layer) about a surface of an aircraft, when the inflow and outflow apparatus is mounted on an aircraft in flight.

13. The inflow and outflow apparatus that is mountable on an aircraft as claimed in claim 12,
wherein the head part has the air inflow on a front end;
wherein the head part encloses a flow duct that is open on both sides, the forward open end of which being the air inflow, and which flow duct in operation is perfused by air and is disposed such that said flow duct in operation runs almost parallel with the flow bearing thereon;
wherein the rearward open end of the flow duct has a smaller cross section than the air inflow;
wherein the inflow and outflow apparatus has a probe heater; and
wherein the probe heater is disposed on an end face of the inflow and outflow apparatus and/or between the air inflow and the inflow line.

14. A water vapor measuring installation, having an inflow and outflow apparatus that is mountable on an aircraft as claimed in claim 12 and a supply line, a measuring system having a measuring chamber and a discharge line, wherein the supply line is tightly connected to the supply line connector of the insert and to an entry of the measuring chamber, and the discharge line is connected to an exit of the measuring chamber and to the discharge line connector of the insert, and wherein the measuring system is configured for determining the water vapor content of air in the measuring chamber.

* * * * *